US 9,394,773 B2

(12) United States Patent
Garcia et al.

(10) Patent No.: US 9,394,773 B2
(45) Date of Patent: Jul. 19, 2016

(54) RESETTABLE BALL SEAT

(75) Inventors: Cesar G. Garcia, Katy, TX (US); Patrick Zimmerman, Houston, TX (US); Charles Parker, Sugar Land, TX (US)

(73) Assignee: Weatherford Technology Holdings, LLC, Houston, TX (US)

( * ) Notice: Subject to any disclaimer, the term of this patent is extended or adjusted under 35 U.S.C. 154(b) by 860 days.

(21) Appl. No.: 13/359,937

(22) Filed: Jan. 27, 2012

(65) Prior Publication Data

US 2013/0192846 A1    Aug. 1, 2013

(51) Int. Cl.
| | |
|---|---|
| *E21B 34/14* | (2006.01) |
| *E21B 43/25* | (2006.01) |
| *E21B 43/12* | (2006.01) |
| *E21B 34/00* | (2006.01) |

(52) U.S. Cl.
CPC .............. *E21B 43/25* (2013.01); *E21B 34/14* (2013.01); *E21B 43/12* (2013.01); *E21B 2034/007* (2013.01)

(58) Field of Classification Search
CPC .... E21B 34/14; E21B 43/14; E21B 2034/007
USPC ............................................. 166/318, 332.4
See application file for complete search history.

(56) References Cited

U.S. PATENT DOCUMENTS

| | | | |
|---|---|---|---|
| 8,356,671 B2 * | 1/2013 | Guillory et al. ............. | 166/318 |
| 2011/0192613 A1 | 8/2011 | Garcia et al. | |
| 2011/0203800 A1 | 8/2011 | Tinker et al. | |
| 2011/0315390 A1 | 12/2011 | Guillory et al. | |
| 2012/0205120 A1 * | 8/2012 | Howell ........................ | 166/373 |

FOREIGN PATENT DOCUMENTS

| | | |
|---|---|---|
| CA | 1285264 A | 6/1991 |
| CN | 102953708 A | 6/2013 |
| CN | 203201542 A | 9/2013 |
| WO | 2010127457 | 11/2010 |
| WO | 2010127457 A1 | 11/2010 |
| WO | 2010127457 A8 | 11/2010 |
| WO | 2011018623 A2 | 2/2011 |

(Continued)

OTHER PUBLICATIONS

Patent Examination Report No. 1 received in corresponding Australian application No. 2012244360, dated Mar. 11, 2014.
Examiner's Requisition received in corresponding Canadian application No. 2,797,457, dated Feb. 28, 2014.

(Continued)

*Primary Examiner* — Robert E Fuller
(74) *Attorney, Agent, or Firm* — Blank Rome, LLP (57) ABSTRACT

A device comprising multiple sliding sleeves actuated using same-sized balls has a resettable seat in an upper sliding sleeve and a non-resettable seat in a lower sliding sleeve. A dropped ball seats on the resettable seat forming a seal. Pressure applied from the surface shifts the resettable seat and an insert. Upon being shifted, the resettable seat releases the ball, which then moves downward to the lower sliding sleeve where the ball lands on the non-resettable seat and shifts the insert. After the first ball is released from the upper sliding sleeve, a biasing device shifts the insert whereby the seat is reset to catch the next ball. A second same-sized ball may then be dropped and land on the now reset first seat to further shift the first insert.

36 Claims, 9 Drawing Sheets (56) References Cited

FOREIGN PATENT DOCUMENTS

| WO | 2011018623 A3 | 2/2011 |
| WO | 2011100748 A2 | 8/2011 |
| WO | 2011100748 A3 | 8/2011 |

OTHER PUBLICATIONS

European Search Report received in European Application No. EP13152166, dated Mar. 12, 2015.
Search Opinion received in European Application No. 13152166.8, dated Mar. 12, 2015.

* cited by examiner

RESETTABLE BALL SEAT

BACKGROUND

As fewer hydrocarbon resources are available and global demand continues to increase, methods and devices to produce hydrocarbons efficiently are becoming increasingly crucial.

One method of increasing efficiency and reducing the cost of producing hydrocarbons is to drill a single wellbore that intercepts many zones. Once the well is drilled it may be necessary to stimulate each zone independently. Typically the stimulation process begins nearest the lower end of the well otherwise known as the toe of the well.

In the past, the process began by drilling a well, during which, the number of formations that are to be stimulated is determined, keeping in mind the upper limit that can be run into a wellbore.

In the past, systems have been used that may have for example, 21 different stages. In turn, each stage needs a different ball size. Typically the lowermost stage will use the smallest ball size and each stage will use progressively larger ball sizes as the stimulation process moves from the toe of the well towards the surface.

When running the twenty one zone system into the formation the various sliding sleeves and zone isolation packers are assembled on the surface, starting with the smallest sliding sleeve at the bottom so that the smallest ball will activate the smallest or lowermost sleeve.

The production tubing is assembled on the surface. At the lowermost end of the tubing may be a fill shoe or it may have a pressure actuated sliding sleeve or toe sleeve. The toe sleeve is typically opened with tubing pressure alone and a ball is not necessary to actuate the sliding sleeve in the toe sleeve. At various intervals along the production assembly, zone isolation devices and corresponding sliding sleeve assemblies may be placed.

Zone isolation may be accomplished by cementing the production tubing and sliding sleeve system into place. Other devices may be used for formation zone isolation such as wellbore packers, including swellable packers, hydraulic control line packers, and mechanically actuated packers.

The zone isolation devices are located along the production assembly both above and below each sliding sleeve corresponding with each formation zone that is going to fraced or produced. Typically a ball actuated sliding sleeve is placed so that it is centrally located in a formation zone. Zone isolation devices are placed so that the production tubing is sealed to the wellbore below the formation zone and above the formation zone. Additionally it may be necessary to place anchoring devices at intervals along the length of the production tubular to prevent movement of the production tubular. Any movement of the production tubular could cause the zone isolation devices to shift so that they are no longer located above and below a formation zone or movement could cause erosion of the isolation packer's seal thereby causing the seal to fail.

Each of the sliding sleeve assemblies starting just above the toe sleeve and moving towards the surface utilizes a successively larger ball.

As the production tubular is assembled it is lowered into the wellbore. In those cases where a fill shoe is used the production tubing may be lowered at any rate that keeps the production tubing at least partially filled in order to reduce the buoyancy of the production tubular. In other instances the toe sleeve may be used to seal the lower end of the production tubular. When the lower end of the production tubular is sealed, mud or other fluid may be pumped into the production tubular from the surface. When the mud or other fluid is pumped into the production tubular from the surface the buoyancy of the production tubular may be controlled. By controlling the production tubular's buoyancy the production tubular may be floated into any relatively long horizontal sections of the wellbore.

Practical issues related to the size of the larger and smaller balls tend to limit the number of sleeves in a system. While referring generally to a ball to engage each seat in the corresponding sliding sleeve, any object such as a dart or plug, that can move through the well and engage the seat in the sliding sleeve may be used.

SUMMARY

A device and method is provided to actuate two or more sliding sleeves utilizing approximately the same sized ball. The device has a resettable seat in the upper sliding sleeve and a non-resettable seat in the lower sliding sleeve. A ball is dropped into a wellbore where it seats on the resettable seat in the upper sleeve forming a seal. Pressure is applied from the surface whereupon the resettable seat and an insert are shifted from a first position to a second position. Upon being shifted from the first position to the second position the resettable seat may release the ball. The ball then moves downward to the lower sliding sleeve where the ball may land upon the non-resettable seat to shift the insert open, sealing the wellbore and allowing the adjacent formation to be fraced. After the first ball is released from the upper sliding sleeve, a biasing device shifts the insert from the second position to a third position where the seat is reset to catch the next ball. A second but approximately same sized ball may then be dropped in to the wellbore where it lands upon the now reset first seat to shift the first insert open and to seal the wellbore whereupon the adjacent formation may be fraced.

DETAILED DESCRIPTION

The description that follows includes exemplary apparatus, methods, techniques, and instruction sequences that embody techniques of the inventive subject matter. However, it is understood that the described embodiments may be practiced without these specific details.

Figure 1:
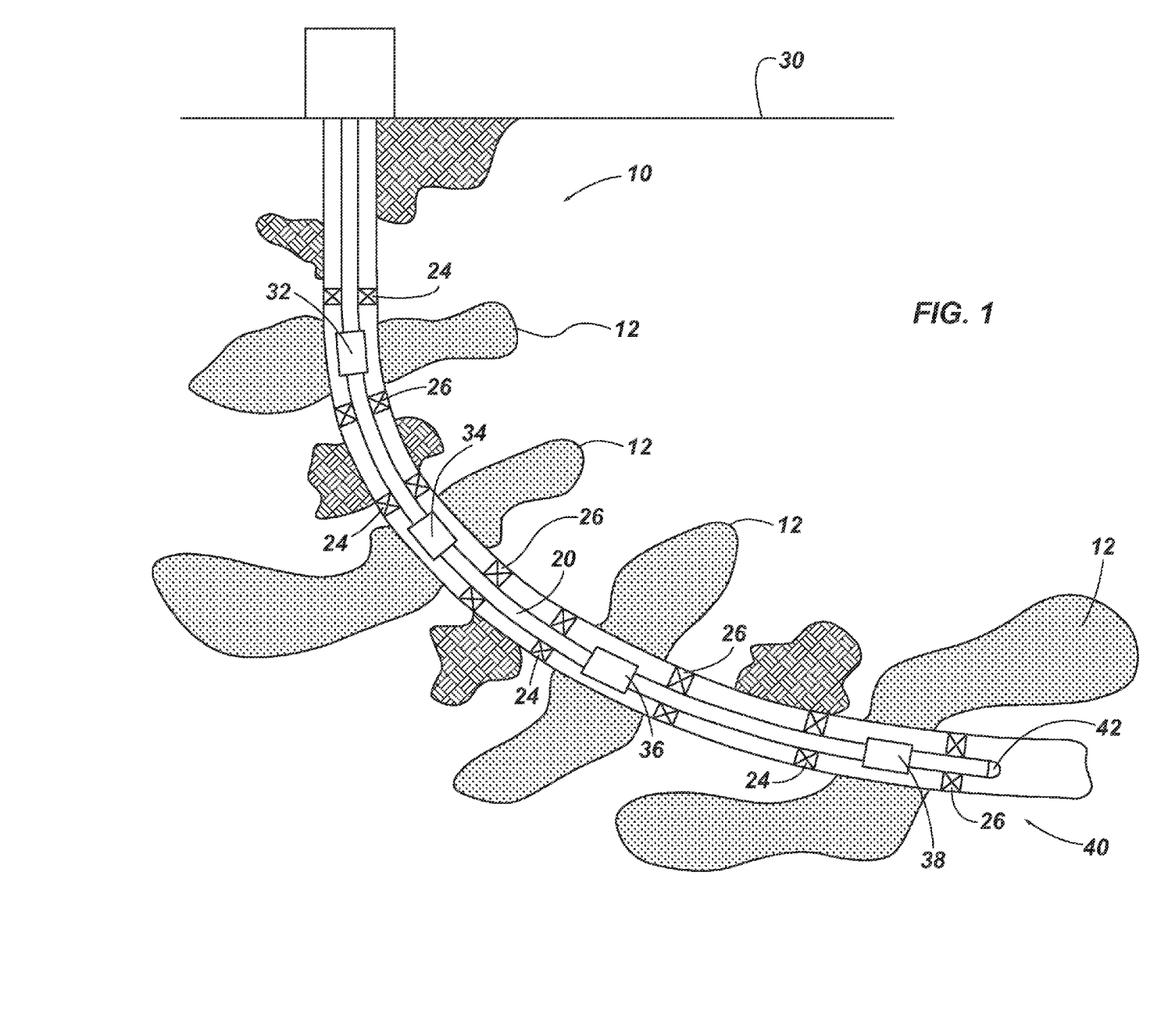
FIG. 1 depicts a schematic view of a well intersecting multiple formation zones.

FIG. 1 depicts a wellbore 10 that intersects several hydrocarbon formations 12. A production tubular 20 is assembled on the surface 30 and lowered into the wellbore 10. The production tubular 20 is assembled so that each sliding sleeve assembly 32, 34, 36, 38 is placed so that it will be adjacent to a formation zone 12. Zonal isolation is accomplished by cementing the production tubular in place or by placing a packer 24 above each formation zone 12 and a packer 26 below each formation zone 12. Typically a toe sleeve 42 is placed at the lowermost end of the production tubular 20.

The production tubular 20 is run into the wellbore 20 until each sliding sleeve assembly 32, 34, 36, 38 is adjacent to its designated formation zone 12. Once the production tubular is in place each packer 24, 26 is set. Once the packers 24, 26 are set the operator may drop the smallest ball. The smallest ball will travel down the interior of production tubular 20 until it lands on a seat in sliding sleeve 38. The operator continues to apply pressure from the surface 30. The pressure will act on the ball and seat in sliding sleeve 38 to shift open an insert in sliding sleeve 38 to allow fluid access from the interior of the production tubular 20 and the formation zone. The ball remains on the seat in sliding sleeve 38 blocking any further fluid flow past the production tubular 20. With formation zone 12 adjacent to the now open sliding sleeve 38 and isolated by packers 24 and 26, fluid flow through the interior of production tubular 20 is blocked. The operator may then begin to stimulate formation zone 12 that is adjacent to sliding sleeve 38.

Once the formation zone 12 adjacent to sliding sleeve 38 is stimulated the operator may then begin operations to stimulate the next higher formation zone 12 adjacent to sliding sleeve 36.

Ball actuated stimulation operations begin at the lowermost formation zone since a large ball will block access to any lower formations.

Figure 2A:
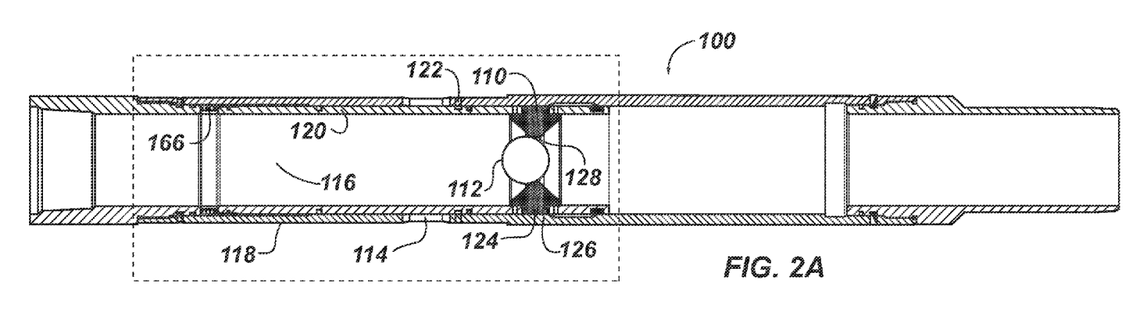
FIG. 2A depicts an upper sliding sleeve with a ball landed in the resettable seat.
Figure 2B:
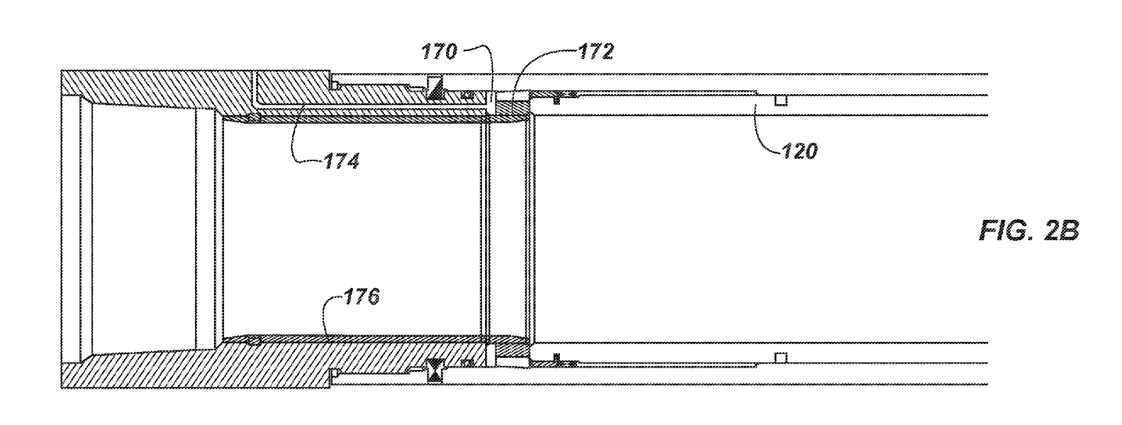
FIG. 2B depicts a fluid pressure bias device for an upper sliding sleeve having a resettable seat.
Figure 2C:
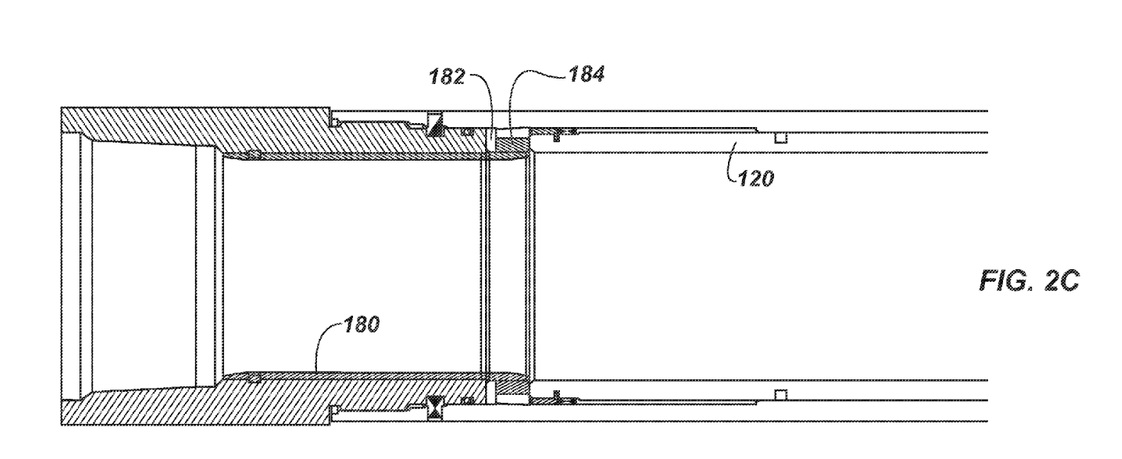
FIG. 2C depicts a gas pressure bias device for an upper sliding sleeve having a resettable seat.
Figure 2D:
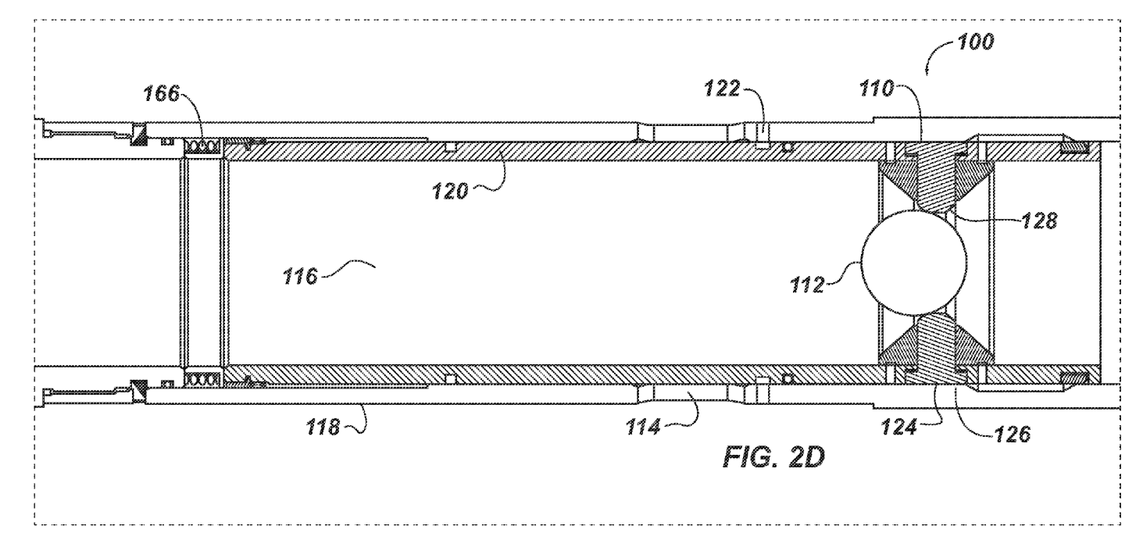
FIG. 2D depicts an enlarged view of a portion of the upper sliding sleeve with a ball landed in the resettable seat as illustrated in FIG. 2A.

FIGS. 2A and 2D depict a sliding sleeve 100 with a resettable seat 110 and insert 120 in the first position. Ball 112 is landed on the resettable seat 110. The resettable seat 110 is linked to insert 120. The sliding sleeve has ports 114 that allow access from the throughbore 116 to the sliding sleeve exterior 118. In position 1 insert 120 blocks fluid access through the port 114 between the throughbore 116 and the exterior of the sliding sleeve 118.

A bias device 166, in FIG. 2 a spring, is shown in its compressed position. Other bias devices known in the industry may be used as well.

FIG. 2B shows a piston 172, such as a hydraulic piston, with a pressure chamber 170 and a pressure supply line 174 that may be used to supply bias force to move the insert 120 from the second position to the third position. Sleeve 176 contains the pressure as the attached pressure piston 172 moves downward.

FIG. 2C shows a piston 184 with a pressure chamber 182 where the pressure chamber is filled with a compressed gas to supply bias force to move the insert 120 from the second position to the third position. Sleeve 180 contains the pressure as the attached piston 184 moves downward.

The resettable seat 110 is shown in a set position where the resettable seat 110 has an interior portion 128 that is capable of retaining an appropriately sized ball such as ball 112. The resettable seat 110 has an exterior portion 124 that is supported by the interior of the sliding sleeve housing 126.

Typically the sliding sleeve 100 is run into the wellbore 10 in a first position with the insert 120 latched into position by a retaining device such as a shear pin 122, a snap ring, or any other device provides sufficient resistance to retain the insert 120.

Once the ball 112 engages the resettable seat 110 the operator may then begin to apply pressure from the surface against the ball 112 and the resettable seat 110. When sufficient pressure is exerted against the ball 112 and the resettable seat 110, then the insert 120, the ball 112, and the resettable seat 110 will all shift together to a second position.

Figure 3A:
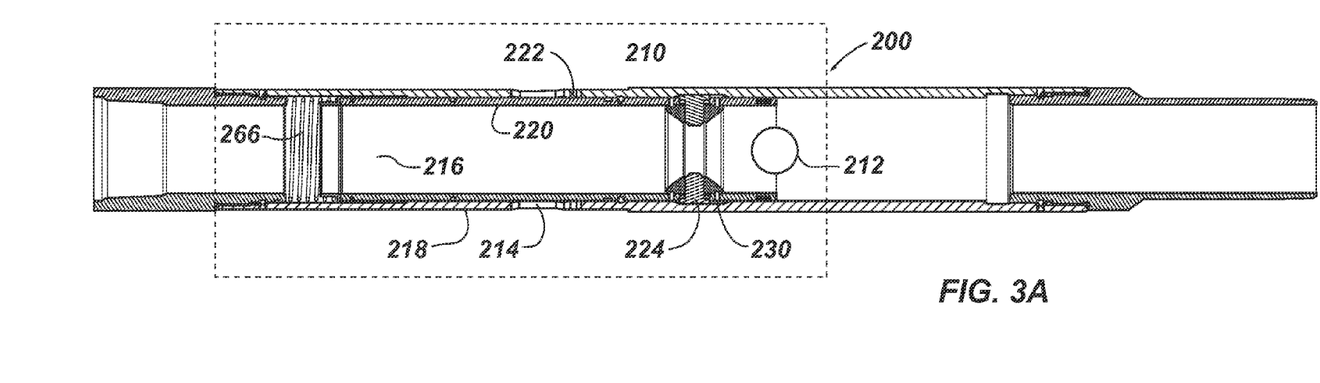
FIG. 3A depicts an upper sliding sleeve with the insert in position 2 and the ball released.
Figure 3B:
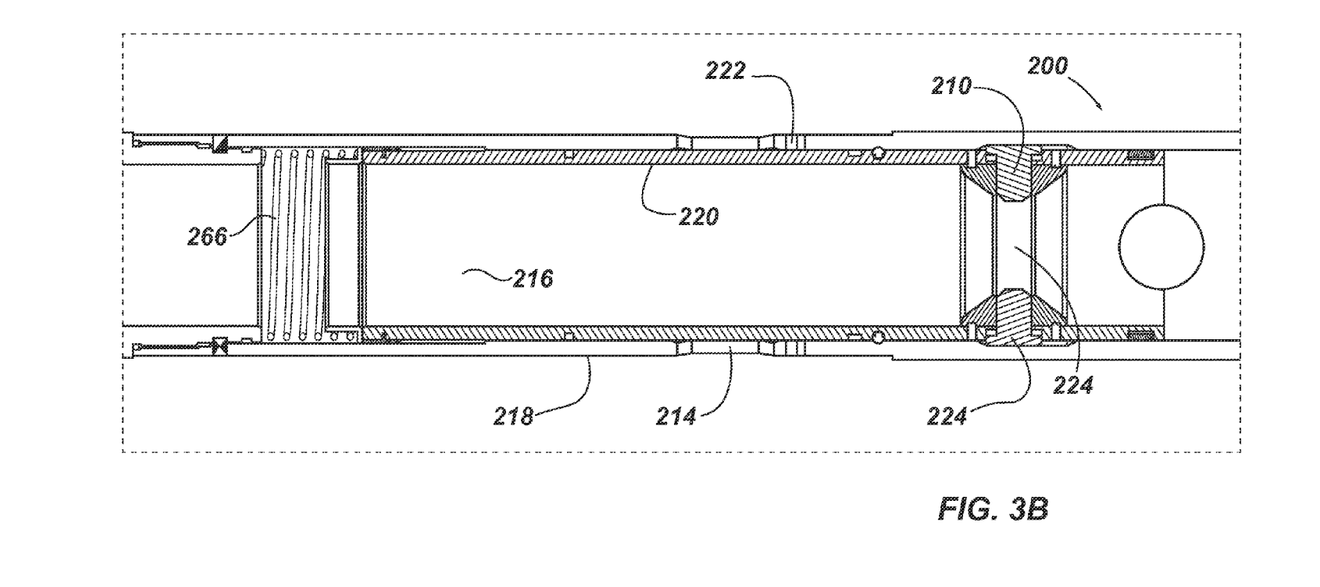
FIG. 3B depicts an enlarged view of a portion of the upper sliding sleeve with the insert in position 2 and the ball released.

FIGS. 3A and 3B depicts a sliding sleeve 200 having a resettable seat 210 and insert 220 in the released or second position. The ball 212 is shown just downstream of resettable seat 210 after it has been released.

Typically, insert 220 is biased so that it may only move downward. Initially retaining device 222 prevents any movement of the insert 222 while bias device 266 prevents any upward movement of the insert 220. The retaining device 222 has been sheared and the insert 220 has moved in the only direction allowed, downward, a small amount to allow the resettable seat 210 to move outward into the recess 230 in the interior of the sliding sleeve housing 126. With the exterior portion 224 of the resettable seat 210 in the recess 230, the interior portion 228 of the resettable seat is no longer capable of retaining the appropriately sized ball 212.

In the second position the insert 220 has moved downward a small amount but not enough to uncover the ports 214. In the second position fluid access from the throughbore 216 to the sliding sleeve exterior 218 is blocked.

In the second position the insert 220 is not restrained from moving in the downward direction. The bias device 266 continues to apply force to the insert 220 causing it to continue to move to the third position. While bias device is shown as a spring any alternative device to apply pressure, such as a hydraulic piston, compressed gas, or hydrostatic pressure, could be used.

Figure 4A:
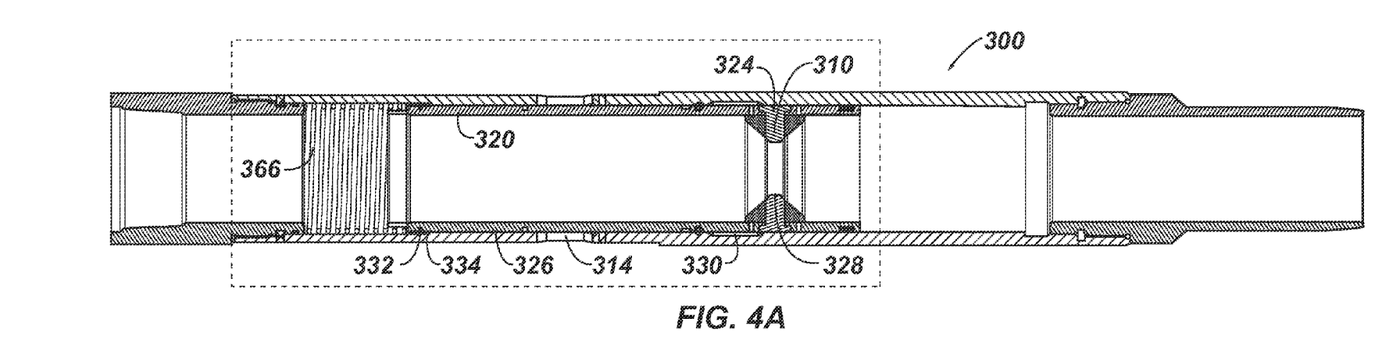
FIG. 4A depicts a upper sliding sleeve with the insert in position 3 and the resettable seat reset.
Figure 4B:
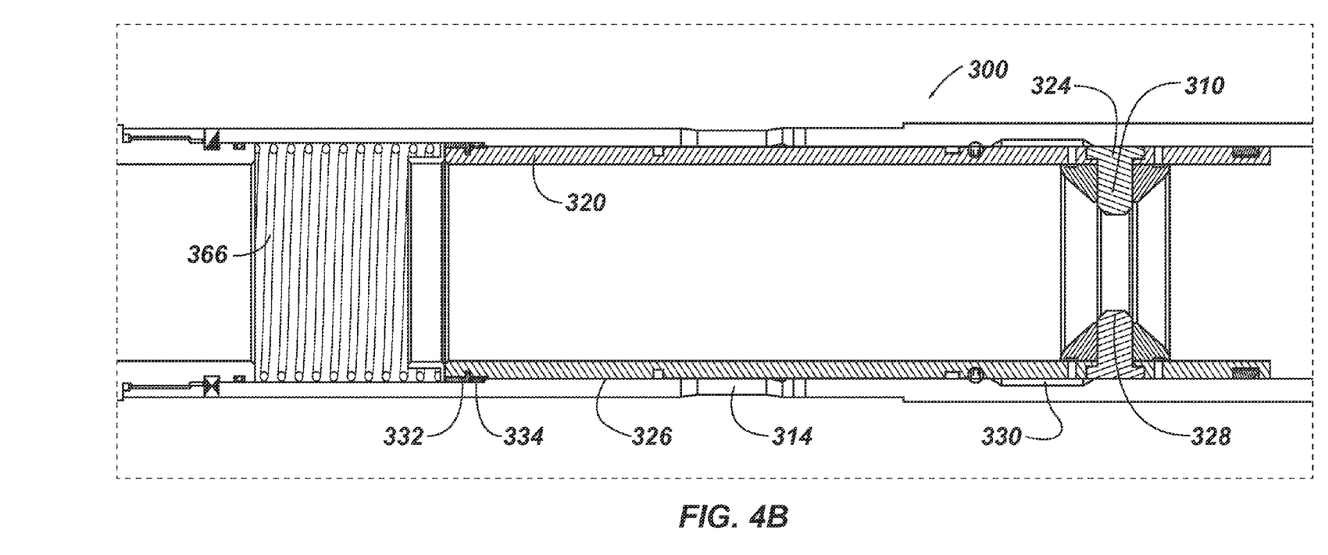
FIG. 4B depicts an enlarged view of a portion of the upper sliding sleeve with the insert in position 3 and the resettable seat reset.

FIGS. 4A and 4B depicts a sliding sleeve 300 having a resettable seat 310 in a reset position and insert 320 in the third position.

In the third position the resettable seat 310 has been reset due to the bias device 366 applying sufficient force to move the insert 320 down to allow a second shear device 332 attached to the insert 320 to come into contact with a shoulder 334 in the interior of the sliding sleeve housing 326. When the second shear device 332 contacts the shoulder 334 further downward movement of the insert 320 ceases.

When the insert 320 moves from the second position to the third position the resettable seat 310 is reset so that it will retain the next appropriately sized ball. As the resettable seat 310 moves downward the exterior portion 324 is forced out of the recess 330 and in towards the center of the sliding sleeve 300 so that the interior portion 328 of the resettable seat is once again capable of retaining an appropriately sized ball.

Figure 5A:
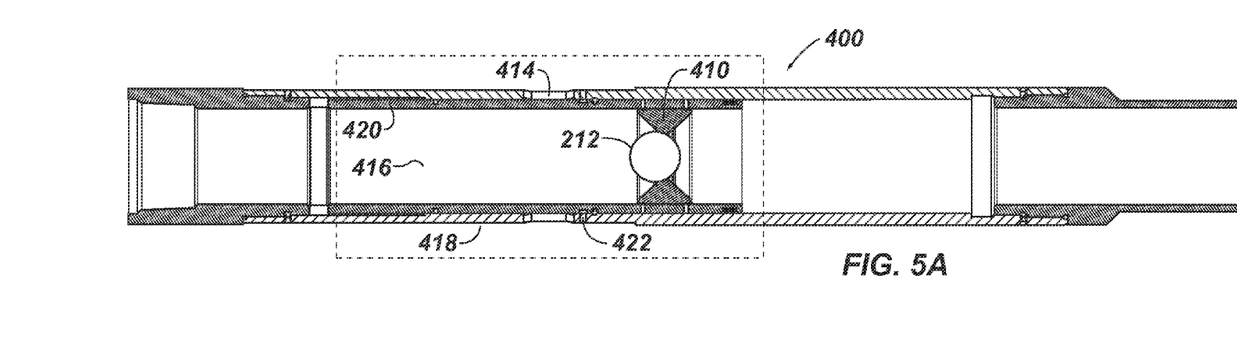
FIG. 5A depicts a lower sliding sleeve with the ball landed on the seat.
Figure 5B:
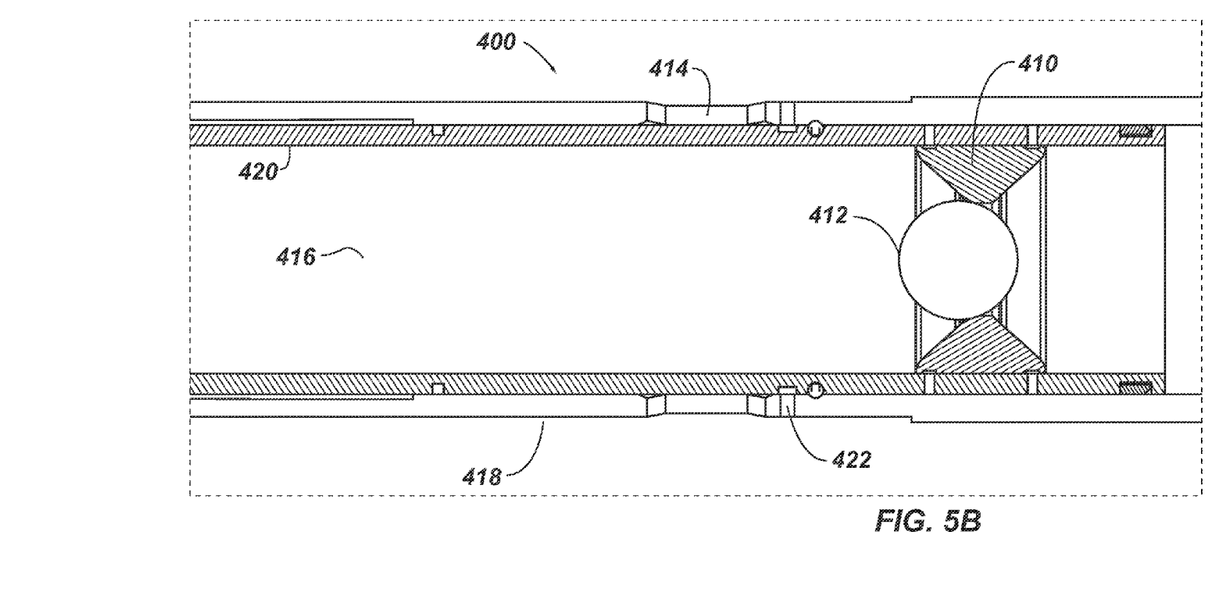
FIG. 5B depicts an enlarged view of a portion of the lower sliding sleeve with the ball landed on the seat.

FIGS. 5A and 5B depict a lower, single shot sliding sleeve 400 with a ball 212. The ball 212 is the same ball that previously moved the upper sliding sleeve's resettable seat from a first position to a second position before the ball 212 was released downhole and landed on seat 410. Seat 410 is linked to insert 420. Sliding sleeve 400 has ports 414 that allow fluid access from throughbore 416 to sliding sleeve exterior 418. In the first position insert 420 blocks fluid access between throughbore 416 and the exterior of sliding sleeve 418.

Typically the sliding sleeve 400 is run into the wellbore in the first position with the insert 420 latched into position by a retaining device such as a shear pin 422, snap ring, or any other device that provides sufficient resistance to retain the insert 420.

As soon as ball 212 engages seat 410 the operator may then begin to apply pressure from the surface against ball 212 and seat 410. When sufficient pressure is exerted against ball 212 and seat 410, insert 420, ball 212, and seat 410 will all shift together to a second position.

Figure 6A:
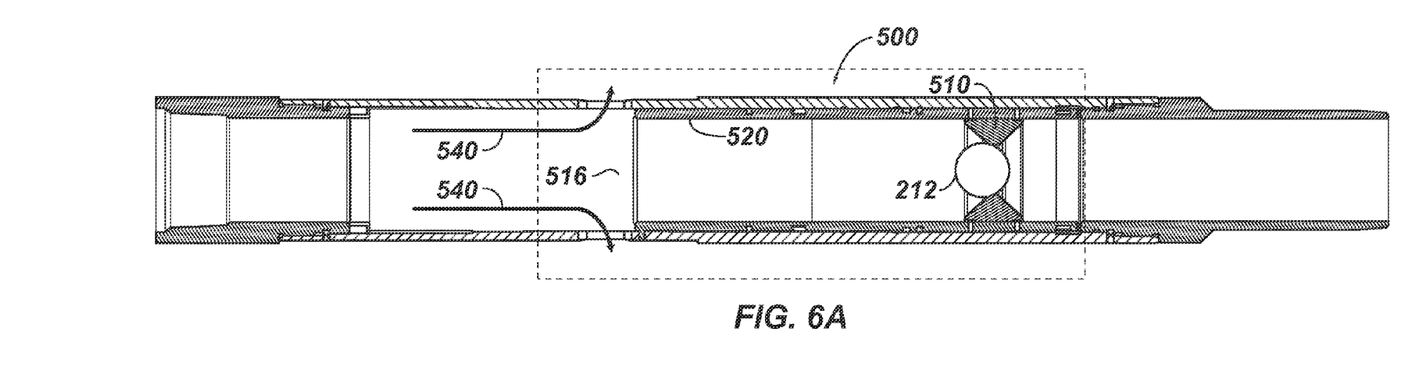
FIG. 6A depicts a lower sliding sleeve with the insert in position 2 and the ball landed on the seat.
Figure 6B:
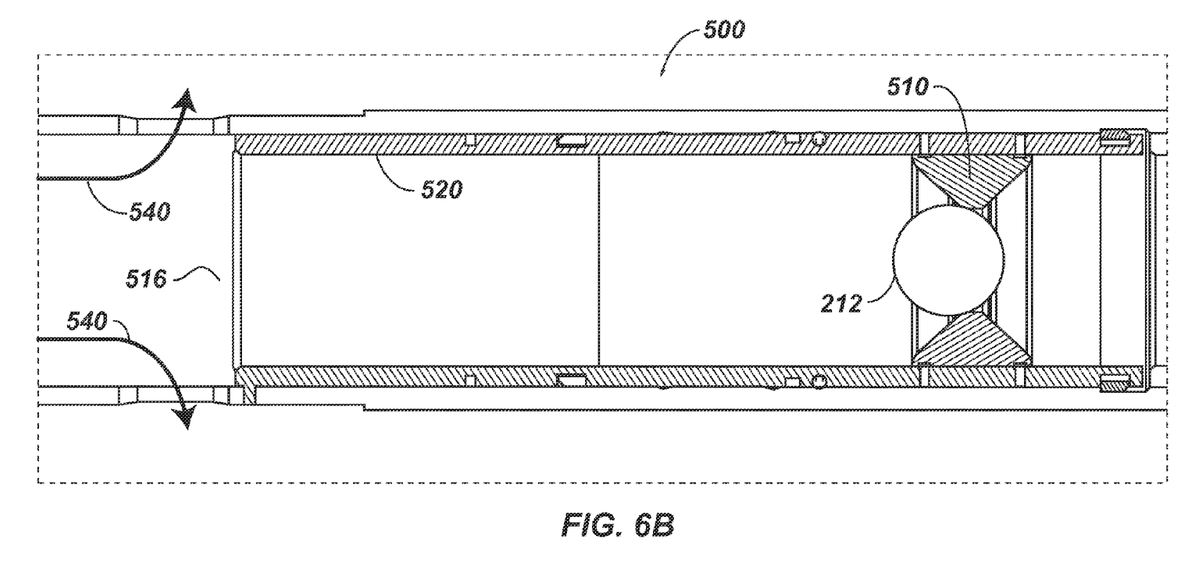
FIG. 6B depicts an enlarged view of a portion of the lower sliding sleeve with the insert in position 2 and the ball landed on the seat.

FIGS. 6A and 6B depicts a lower, single shot sliding sleeve 500 with a ball 212 landed on the seat 510. As shown the insert 520 is in the second position. In the second position the ball 212 on seat 510 prevents fluid from traveling downward and diverts the fluid traveling down the throughbore out to the exterior of the sliding sleeve 518 as shown by arrows 540. By diverting fluid flow 540 from the throughbore 516 to the exterior of the sliding sleeve 518 and blocking fluid flow through the throughbore 516 past the ball 212 and seat 510, the adjacent formation zone may now be stimulated.

Figure 7A:
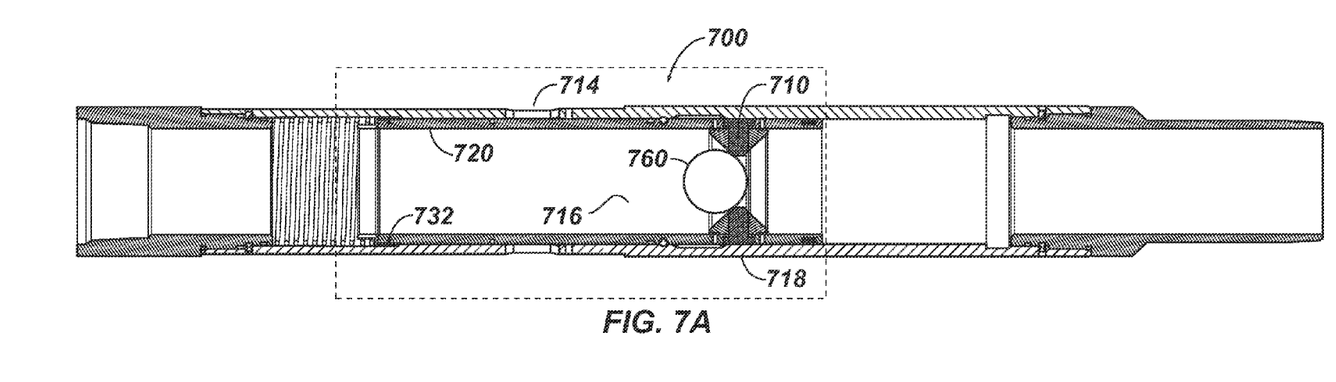
FIG. 7A depicts an upper sliding sleeve with the insert in position 3 and ball landed on the resettable seat.
Figure 7B:
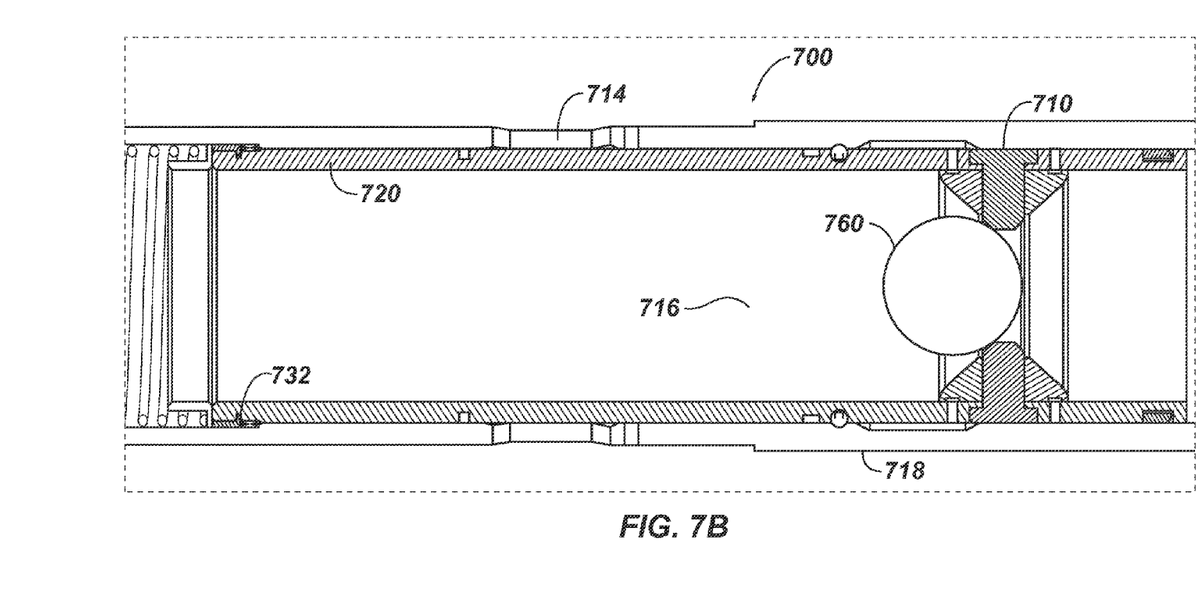
FIG. 7B depicts an enlarged view of a portion of the upper sliding sleeve with the insert in position 3 and ball landed on the resettable seat.

Once the formation adjacent to the lower sliding sleeve 510 has been stimulated a second ball, approximately the same size as the first ball, may be pumped down to land on the partially actuated, but with the ports still blocked, upper sliding sleeve as shown in FIG. 7.

FIGS. 7A and 7B depict an upper sliding sleeve 700 with the insert 720 in position 3 and ball 760 landed on the resettable seat 710. The ball 760 is approximately the same size ball that previously moved the upper resettable seat from a first position to a second position before the ball was released downhole and actuated the lower sliding sleeve. The seat 710 is linked to insert 720. The sliding sleeve 700 has ports 714 that allow fluid access from the throughbore 716 to the sliding sleeve exterior 718. In the third position insert 720 blocks fluid access between the throughbore 716 and the exterior of the sliding sleeve 718.

When the ball 760 seats the operator will see an increase in pressure and may then begin to increase the pressure from the surface against the ball 760 and the seat 710. When sufficient pressure is exerted against the ball 760 and the seat 710 then the second shear device 732 will shear allowing the insert 720, the ball 760, and the seat 710 to shift together into a fourth position.

Figure 8A:
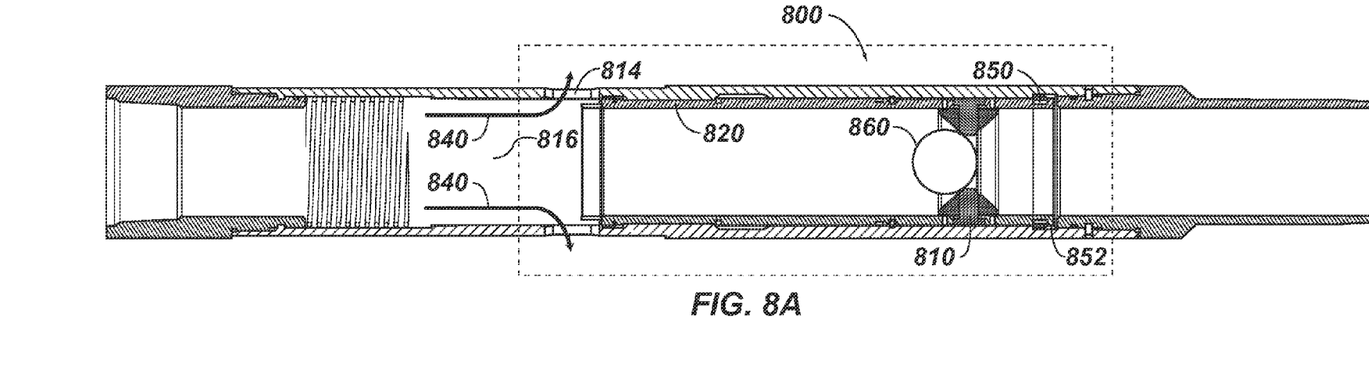
FIG. 8A depicts an upper sliding sleeve with the insert in position 4.
Figure 8B:
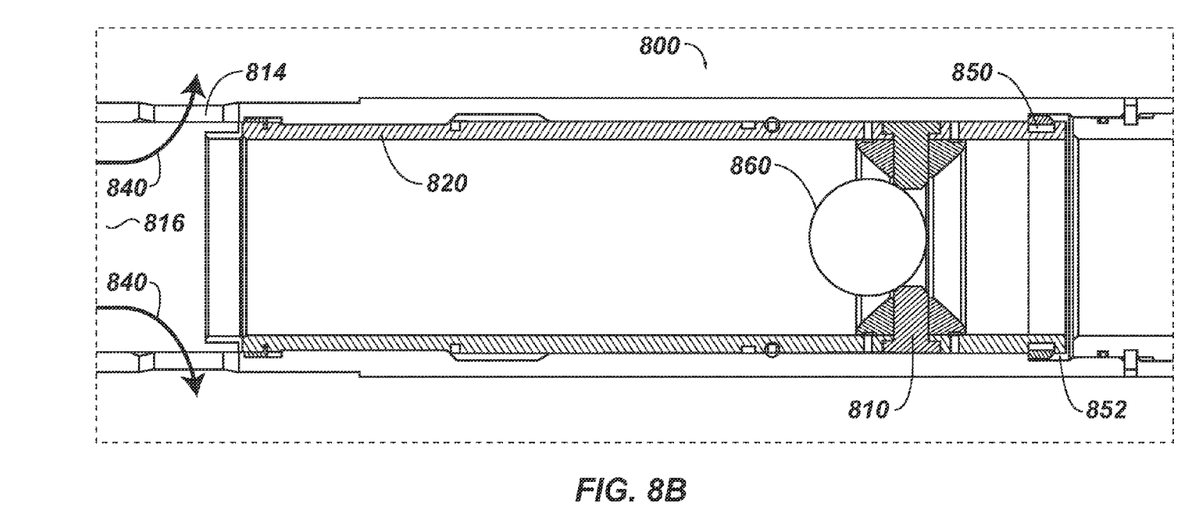
FIG. 8B depicts an enlarged view of a portion of the upper sliding sleeve with the insert in position 4.

FIGS. 8A and 8B depicts an upper sliding sleeve 800 with the insert 820 in a fourth position where ball 860 remains on the resettable seat 810 forming a seal with the resettable seat 810 that blocks fluid flow downward past the upper sliding sleeve 800.

In the fourth position the ball 860 on resettable seat 810 prevents fluid from traveling downward and diverts the fluid traveling down throughbore 816 out to the exterior of the sliding sleeve 818 as shown by arrows 840. By diverting fluid flow 840 from the throughbore 816 to the exterior of the sliding sleeve 818 and blocking fluid flow through the throughbore 816 past the ball 860 and resettable seat 810 the adjacent formation zone may now be stimulated.

The insert 810 is locked into the fourth position by lock 850 that engages with another recess 852. The lock 850 prevents fluid flow from below the well from causing the insert 820 to move back towards the top of the well where the insert 820 might block fluid flow through ports 814.

While the embodiments are described with reference to various implementations and exploitations, it will be understood that these embodiments are illustrative and that the scope of the inventive subject matter is not limited to them. Many variations, modifications, additions and improvements are possible. For example, the implementations and techniques used herein may be applied to any downhole tool that may be actuated by a ball or other flow blocking device.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

What is claimed is:

1. A downhole valve system comprising:
a first sliding sleeve further comprising:
   a first housing having a first outer diameter, a first throughbore, and a first housing port to allow fluid communication between the first throughbore and the first outer diameter;
   an first insert located inside of the throughbore and including a resettable seat, the first insert being movable from a first position, to a second position, to a third position, to a fourth position, wherein the first insert blocks the first housing port in the first, second, and third positions, and wherein the first insert does not block the first housing port in the fourth position; and
   a bias device engaging the first housing and the first insert;
   wherein:
   in the first position the resettable seat is configured to engage with a first ball pumped through the first sliding sleeve to move the first insert between the first position and the second position;
   in the second position the resettable seat is configured to release the first ball, permitting movement of the first insert from the second to the third position by the bias device;
   in the third position the resettable seat is configured to engage with a second ball, substantially the same size as the first ball, pumped through the first sliding sleeve to move the first insert from the third position to the fourth position; and
   in the fourth position the resettable seat is configured to retain the second ball to divert fluid through the first housing port; and
a second sliding sleeve further comprising:
   a second housing having a second outer diameter, a second throughbore, and a second housing port to allow fluid communication between the second throughbore and the second outer diameter;
   an second insert located inside of the second throughbore and a non-resettable seat;
   wherein, in a first position the non-resettable seat is configured to engage with the first ball to move the second insert between a first position in which the second insert blocks the second housing port and a second position in which the second insert does not block the second housing port.

2. The apparatus of claim 1, wherein the bias device is a hydraulic piston.

3. The apparatus of claim 1, wherein the bias device is a spring.

4. The apparatus of claim 1, wherein the bias device is compressed gas.

5. The apparatus of claim 1, where the bias is in the downward direction.

6. The apparatus of claim 1, where the first sliding sleeve first insert and the second sliding sleeve second insert are biased downward.

7. The apparatus of claim 1, wherein the first ball engages the non-resettable seat in the second sliding sleeve to move the second insert between the first position in which the second insert blocks the second housing port and the second position in which the second insert does not block the second housing port, wherein a lock engages the second insert.

8. The apparatus of claim 7, wherein the lock is a snap ring.

9. The apparatus of claim 1 wherein the first ball engages the non-resettable seat in the second sliding sleeve and blocks downward fluid flow.

10. The apparatus of claim 1 wherein the second ball engages the resettable seat in the first sliding sleeve and blocks downward fluid flow.

11. The apparatus of claim 1, wherein at least one of the first insert and the second insert has an insert port to allow fluid communication between a corresponding outer diameter and a corresponding throughbore.

12. The apparatus of claim 11, wherein the first ball engages at least one of the resettable seat or the non-resettable seat to move a corresponding insert between the corresponding first position and the corresponding second position, wherein the corresponding housing port and the corresponding insert port are at least partially aligned to allow fluid communication between the corresponding throughbore and the corresponding outer diameter.

13. The apparatus of claim 1, wherein the second ball size is within about ⅛ of an inch in diameter of the first ball.

14. A sliding sleeve comprising:
a housing having an outer diameter, a throughbore, and a housing port allowing fluid communication between the throughbore and the outer diameter;
an insert located inside of the throughbore and including a resettable seat, the insert being movable from a first position, to a second position, to a third position, to a fourth position, wherein the insert blocks the housing port in the first, second, and third positions, and wherein the insert does not block the housing port in the fourth position; and
a bias device engaging the housing and the insert;
wherein:
in the first position the resettable seat is configured to engage with a first ball pumped through the sliding sleeve to move the insert between the first position and the second position;
in the second position the resettable seat is configured to release the first ball, permitting movement of the insert from the second to the third position by the bias device;
in the third position the resettable seat is configured to engage with a second ball, substantially the same size as the first ball, pumped through the sliding sleeve to move the insert from the third position to the fourth position; and
in the fourth position the resettable seat is configured to retain the second ball to divert fluid from through the housing port.

15. The apparatus of claim 14, wherein the bias device is a hydraulic piston.

16. The apparatus of claim 14, wherein the bias device is a spring.

17. The apparatus of claim 14, wherein the bias device is compressed gas.

18. The apparatus of claim 14, wherein the insert has an insert port alignable with the housing port to allow fluid communication between the outer diameter and the throughbore.

19. The apparatus of claim 18, wherein in at least one of the second and third positions, the housing port and the insert port are at least partially aligned to allow fluid communication between the throughbore and the outer diameter.

20. The apparatus of claim 14, wherein the second ball size is within about ⅛ of an inch in diameter of the first ball.

21. The sliding sleeve of claim 14 wherein:
when the insert is in the first position the resettable seat has a first inner diameter;
when the insert is in the second position the resettable seat has a second inner diameter greater than the first inner diameter;
when the insert is in the third position the resettable seat has a third inner diameter substantially the same as the first inner diameter; and
when the sleeve insert is in the fourth position the resettable seat has a fourth inner diameter substantially the same as the first and third inner diameters.

22. The apparatus of claim 21, wherein the bias device is a hydraulic piston.

23. The apparatus of claim 21, wherein the bias device is a spring.

24. The apparatus of claim 21, wherein the bias device is compressed gas.

25. The apparatus of claim 21, wherein the insert has an insert port alignable with the housing port to allow fluid communication between the outer diameter and the throughbore.

26. The apparatus of claim 25, wherein in at least one of the second and third positions, the housing port and the insert port are at least partially aligned to allow fluid communication between the throughbore and the outer diameter.

27. The apparatus of claim 21, wherein the second ball size is within about ⅛ of an inch in diameter of the first ball.

28. A method to actuate a tool comprising:
landing a first ball on a resettable first seat in a first tool;
shifting a sleeve in the first tool from a first position to a second position;
releasing the first ball from the first tool;
shifting the sleeve in the first tool from the second position to a third position with a biasing device;
landing the first ball on a second seat in a second tool;
shifting a sleeve in the second tool from a first position to a second position;
landing a second ball, approximately the same size as the first ball, on the resettable first seat; and
shifting the sleeve in the first tool from the third position to a fourth position.

29. The method of claim 28 wherein the bias device is a hydraulic piston.

30. The method of claim 28 wherein the bias device is a spring.

31. The method of claim 28 wherein the bias device is compressed gas.

32. The method of claim 28 wherein shifting the sleeve in the first tool from the first position to the second position does not open a flow path from an interior of the first tool to an exterior of the first tool.

33. The method of claim 28 wherein shifting the sleeve in the first tool from the second position to the third position does not open a flow path from an interior of the first tool to an exterior of the first tool.

34. The method of claim 28 wherein shifting the sleeve in the first tool from the third position to the fourth position opens a flow path from an interior of the first tool to an exterior of the first tool.

35. The method of claim 28 wherein shifting the sleeve in the second tool from the first position to the second position opens a flow path from an interior of the second tool to an exterior of the second tool.

36. The method of claim 28 wherein the first ball is not released by the second seat in the second tool in a downward direction.

\* \* \* \* \*